(12) United States Patent
Siegel

(10) Patent No.: US 7,160,287 B1
(45) Date of Patent: Jan. 9, 2007

(54) APPARATUS AND METHOD FOR PERFORMING RADIATION ENERGY TREATMENTS

(75) Inventor: Jerry Siegel, P.O. Box 7662, Delray Beach, FL (US) 33445-7662

(73) Assignee: Jerry Siegel, Northfield, OH (US)

( * ) Notice: Subject to any disclaimer, the term of this patent is extended or adjusted under 35 U.S.C. 154(b) by 148 days.

(21) Appl. No.: 10/227,106

(22) Filed: Aug. 23, 2002

Related U.S. Application Data

(60) Provisional application No. 60/314,938, filed on Aug. 23, 2001.

(51) Int. Cl.
*A61M 5/02* (2006.01)

(52) U.S. Cl. .......................................... 606/3

(58) Field of Classification Search .................... 606/3, 606/7, 10–17; 607/88–93; 372/22–25
See application file for complete search history.

(56) References Cited

U.S. PATENT DOCUMENTS

| | | | | |
|---|---|---|---|---|
| 769,581 A | * | 9/1904 | Arnold | 607/80 |
| 4,719,912 A | * | 1/1988 | Weinberg | 606/4 |
| 4,799,754 A | * | 1/1989 | Goldenberg | 385/33 |
| 4,930,504 A | * | 6/1990 | Diamantopoulos et al. | 607/88 |
| 5,150,704 A | * | 9/1992 | Tatebayashi et al. | 607/89 |
| 5,192,278 A | * | 3/1993 | Hayes et al. | 607/89 |
| 5,755,752 A | * | 5/1998 | Segal | 607/89 |
| 5,830,208 A | * | 11/1998 | Muller | 606/7 |
| 5,982,789 A | * | 11/1999 | Marshall et al. | 372/25 |
| 6,280,438 B1 | * | 8/2001 | Eckhouse et al. | 606/9 |
| 6,391,021 B1 | * | 5/2002 | Mueller et al. | 606/7 |

* cited by examiner

*Primary Examiner*—David M. Shay
(74) *Attorney, Agent, or Firm*—Renner, Otto, Boisselle & Sklar, LLP

(57) ABSTRACT

An apparatus and method to apply photo-stimulation, photodynamic therapy and/or ablation laser treatment to biological tissue. The apparatus includes a plurality of radiation energy sources, preferably laser beams. Additionally, the apparatus allows either a single wavelength or a combination of various wavelengths, either coincidentally or adjacently, to be utilized to achieve a desired treatment effect. Laser beams are transmitted to the treatment area by one or more fiber optic cables which terminate at an assembly structured to collimate the emitted radiation prior to application to the tissue. In addition, the apparatus includes a focal length setting mechanism which assures that a constant, fixed distance exists between the point of discharge of the laser beam and the biological tissue, thus assuring a constant energy density at the point of application. A method is presented for applying photo-stimulation, photocollagen stimulation and/or ablation laser treatment utilizing the above apparatus.

1 Claim, 12 Drawing Sheets

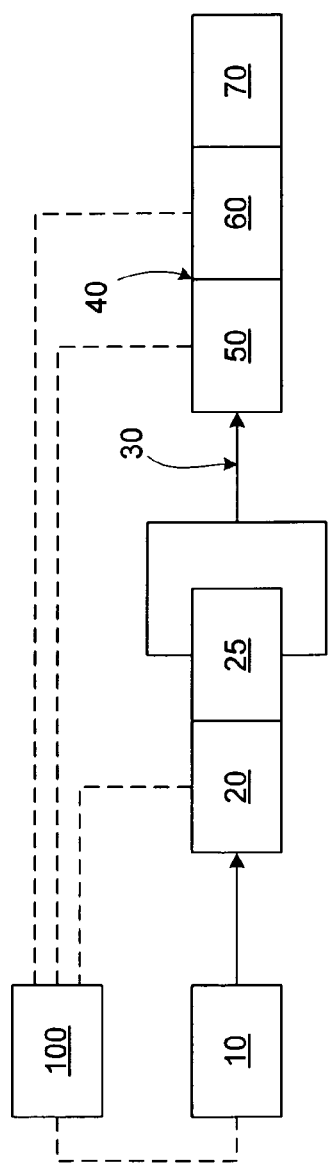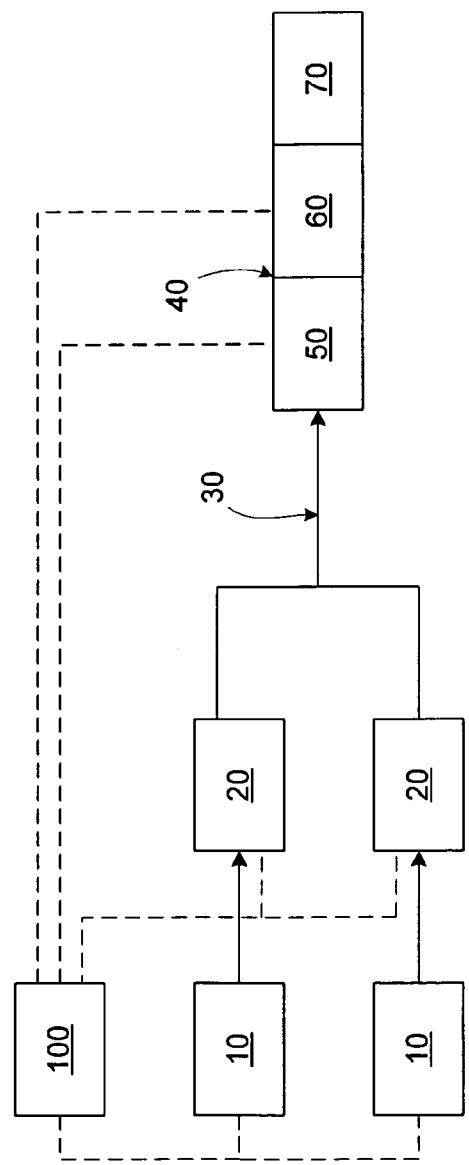

Laser Control Screen

Patients Name -------------------- John Smith
Malady ------------------- Muscular Dystrophy
Time of Treatment ------------------- 2:00PM

---

Treatment Modality ------------ Biostimulation

Treatment Protocol --------- Muscular Dystrophy

---

Dosage Settings

Power -------------------- 15,000 milliwatts
Type of Cycle --------------- 50% Duty Cycle
Cadence ------------------------------ None
Joules -------------------------------- 2,000
Time --------------------------------- 20:00
Spot Size ------------------------------ 8Cm²
Energy Density ------------------ 1500J/Cm²

---

Emitted Dosage

Joules ---------------------------------- 1000
Energy Density --------------------- 1500j/Cm²
Time ---------------------------------- 10:00

---

Delivered Dosage

Joules ---------------------------------- 2000
Energy Density --------------------- 1500j/Cm²
Time ---------------------------------- 20:00

---

Laser Status

Stopped
Armed
Running

FIG. 11

| Power | Area | | Power Density |
|---|---|---|---|
| 1 W / | 0.67 cm$^2$ | = | 1500 mW/cm$^2$ |
| 2 W / | 1.33 cm$^2$ | = | 1500 mW/cm$^2$ |
| 3 W / | 2.00 cm$^2$ | = | 1500 mW/cm$^2$ |
| 4 W / | 2.68 cm$^2$ | = | 1500 mW/cm$^2$ |
| 5 W / | 3.34 cm$^2$ | = | 1500 mW/cm$^2$ |
| 6 W / | 4.00 cm$^2$ | = | 1500 mW/cm$^2$ |
| 7 W / | 4.67 cm$^2$ | = | 1500 mW/cm$^2$ |
| 8 W / | 5.33 cm$^2$ | = | 1500 mW/cm$^2$ |
| 9 W / | 6.00 cm$^2$ | = | 1500 mW/cm$^2$ |
| 10 W / | 6.67 cm$^2$ | = | 1500 mW/cm$^2$ |

FIG. 13

| Power | Time | Area | | Energy Density |
|---|---|---|---|---|
| 1 W x | 900s / | 0.60 cm$^2$ | = | 1500 J/cm$^2$ |
| 2 W x | 900s / | 1.20 cm$^2$ | = | 1500 J/cm$^2$ |
| 3 W x | 900s / | 1.80 cm$^2$ | = | 1500 J/cm$^2$ |
| 4 W x | 900s / | 2.40 cm$^2$ | = | 1500 J/cm$^2$ |
| 5 W x | 900s / | 3.00 cm$^2$ | = | 1500 J/cm$^2$ |
| 6 W x | 900s / | 3.60 cm$^2$ | = | 1500 J/cm$^2$ |
| 7 W x | 900s / | 4.20 cm$^2$ | = | 1500 J/cm$^2$ |
| 8 W x | 900s / | 4.80 cm$^2$ | = | 1500 J/cm$^2$ |
| 9 W x | 900s / | 5.40 cm$^2$ | = | 1500 J/cm$^2$ |
| 10 W x | 900s / | 6.00 cm$^2$ | = | 1500 J/cm$^2$ |
| 11 W x | 900s / | 6.60 cm$^2$ | = | 1500 J/cm$^2$ |
| 12 W x | 900s / | 7.20 cm$^2$ | = | 1500 J/cm$^2$ |
| 13 W x | 900s / | 7.80 cm$^2$ | = | 1500 J/cm$^2$ |
| 14 W x | 900s / | 8.40 cm$^2$ | = | 1500 J/cm$^2$ |
| 15 W x | 900s / | 9.00 cm$^2$ | = | 1500 J/cm$^2$ |

FIG. 14

APPARATUS AND METHOD FOR PERFORMING RADIATION ENERGY TREATMENTS

This application relates back to Provisional Patent Application jc879 U.S.PTO 60/314,938—Filed on Aug. 23, 2001

BACKGROUND OF THE INVENTION

1. Field of the Invention

The present invention is directed to an apparatus and a method for performing radiation energy treatment on a target area of biological tissue, wherein the apparatus for performing radiation energy treatments on biological tissue is structured to provide a plurality of laser energy treatments comprising of at least but not limited to ablation, biostimulation, photo-stimulation, photocollegan regeneration, and photo-dynamic therapy, either separately or in conjunction with one another, utilizing low, medium, and/or high power lasers employing either a single wavelength or combining various wavelengths, either coincidentally or adjacently, for a specific desired effect in a safe and controlled manner that allows for a larger and more effective contact area to be defined by effectively controlling the energy density of the radiation energy affecting the biological tissue. Furthermore the present invention is configured to use low, medium, and high power laser in order to permit the practitioner to switch from an ablative treatment modalities to another non-ablative treatment modality safely by adjusting various parameters of the laser beam precisely to maintain a desired energy density. Additionally, the present invention employs a unique construction technique which significantly reduces the physical size of the operative unit thereby facilitating the ease and accuracy of employing the apparatus for performing radiation energy treatment utilizing a plurality of treatment regimens.

2. Description of the Related Art

The use of radiation energy in medical treatment equipment and methods remains a relatively new and expanding area of technology. However, certain applications of radiation energy are well known in the medical field. Of particular interest is the use of the radiation energy generated by a laser beam. Laser energy has been utilized for a variety of medical applications ranging from the relief of pain and stiff joints to the acceleration of the healing process and the reduction of scarring and ulcers of the skin. The former applications require exposing the treatment area to an amount of low level laser energy in a process commonly referred to as photo-stimulation. As the name suggests, the purpose of photo-stimulation is the stimulation and promotion of cellular material growth. The latter applications require the application of larger amounts of medium to high level laser energy, in another process commonly referred to as ablation, wherein the laser energy results in significant removal or destruction of the targeted tissue. Photocollegean regeneration is another non-ablative laser treatment modality wherein, wrinkles and stretch marks are reduced by the biological tissue response to certain types of laser radiation whereby there is of an increase in vasodilatation, ATP, and collagen production.

Each treatment regimen requires different radiation energy wavelengths with different absorption characteristics to be most effective for a specific result or treatment. Due to the different energy level and wavelength requirements between the photo-stimulation, photocollegean, biostimulation and ablation processes, separate laser energy sources and exposure apparatus are typically employed to perform each treatment process.

To date, control of the amount of energy to which biological tissue is exposed has been less than precise. This is due in part to the variable nature of the laser energy sources, as well as the variability in the biological tissue to be exposed, specifically, the interaction between the absorption characteristics of a specific wavelength within the electromagnetic spectrum in relation to the various properties of the tissue being irradiated. In addition, the variability of the composition within the biological tissue to be exposed, specifically, the differences in the absorption characteristics between the various components of the tissue (i.e. the types of cells, organelles, organs, etc.). With regard to laser energy sources, the main variables are the radiation energy output, the time of exposure, and the contact area, which define the energy density at the point of exposure of the biological tissue, and the radiation energy wavelength. For example, a laser which generates a particular radiation energy output, may generate that energy at any one of a number of different energy wavelengths. The energy wavelength is, at least in part, a function of the base material or materials utilized to generate the laser beam. Although the same radiation energy output may be generated by different laser beams, their usefulness for a particular medical application may be widely varied. This is due to the fact that different energy wavelengths affect biological functions in different ways. Therefore, not only must the treatment area be exposed to the correct amount of laser energy, the energy wavelength must be appropriate for the desired effect to be achieved.

In addition to the variability present in laser energy output and energy wavelength, perhaps the most critical variable in the medical application of laser beams, and among the most difficult to accurately control, is the energy density at the point of exposure of the biological tissue. The energy density is typically defined in terms of either milliwatt-seconds per square centimeter ("mW-s/$cm^2$") or joules per square centimeter ("J/$cm^2$"), wherein one thousand milliwatts times one second equals one joule, and as indicated, the energy density represents the quantity of energy imparted to a specific area. Thus, the energy density is defined by the combination of the energy output of the laser beam, the time of exposure and the size of the area of biological tissue exposed to the laser beam, which is further a function of the distance of the laser beam from the surface exposed.

However, modern medical laser treatment equipment often employs a wand-like device which is moveably positioned and directed at an area of biological tissue by the laser operator. Even in the hands of the skilled medical laser operator, however, the distance and angle between the discharge end of such wand-like devices and the surface exposed are not precisely maintained, therefore, the area exposed to the laser energy often varies. This variability in the area exposed results in a variable energy density to which the biological tissue is exposed. Further, even when a fixed laser beam is employed, control of the area exposed is difficult and imprecise. First, the patient must be positioned the exact and correct distance from the laser beam to define the area of exposure, which is difficult to do with precision due to the distance between the laser beam and the patient. In addition, the patient must be positioned such that the area exposed is at the correct angle relative to the fixed laser beam, again being difficult to do with precision due to the distance between them. Further, even assuming that the patient is placed at the exact and correct distance and at the exact and correct angle from a fixed laser beam, the patient must remain in that exact position for the duration of the time of exposure. As may be appreciated, the control of the area exposed, and thus, the energy density to which biological tissue is exposed, by either of the above techniques is difficult at best. Indeed, partly for this reason, known systems are configured to only treat very small areas, making the procedures very time consuming and as a result, more susceptible to error.

Therefore, it would be desirable to provide a single apparatus for performing photo-stimulation, and/or ablation laser treatment having a variety of radiation energy sources to provide low, medium, and/or high power laser beams. It would also be advantageous to provide an apparatus for performing photo-stimulation, biostimulation, photocollagen stimulation, and/or ablation laser treatment having a variety of laser beam sources to provide a range of energy wavelengths which may be utilized for a variety of different treatments, either separately or simultaneously. Another benefit would be to provide an apparatus that permits the precise control of the radiation's beams properties. By providing a means to precisely control the properties of the radiation beam and by controlling the energy density at the point of exposure to the biological tissue this apparatus allows for higher wattage's, greater variety of treatment modalities and larger treatment areas to be employed, while providing a safe, accurate and effective method of performing radiation energy treatments. Furthermore, it would be helpful to provide an apparatus having an operative unit significantly reduced in size to permit greater ease in employing the apparatus and thereby increasing the safety, accuracy and effectiveness of the method for performing radiation energy treatment with the apparatus.

While there is prior art that exists regarding the use of laser therapies in medical conditions, no one has described or suggested an apparatus that can emit either a single wavelength or a plurality of individual wavelengths wherein the wavelengths can either be utilized individually or combined into a single therapeutic beam of radiation and can control said radiation's absorption properties, energy density, and depth penetration, so that a practitioner skilled in the art can perform either, photo-stimulation, photocollegan regeneration, or a plurality of therapeutic biostimulating treatments on a variety of different types of tissue, with the same apparatus. Furthermore, no one has described an apparatus that incorporates a device that comprises a collector with a reflecting lens that collects and then redirects the scattered and reflected radiation back to the site of treatment while utilizing either a single collimator or multiple collimators that are targetable and focusable and that include an adjustable focal length mechanism that emit coincident visible and infrared radiation, that can either intersect inside the targeted tissue or deploy in series upon the tissue, wherein the infrared radiation has a wavelength of approximately 1110 nm.

SUMMARY OF THE INVENTION

The present invention is directed to an apparatus and a method for performing non-invasive and invasive radiation energy treatments, including at least photo-stimulation, biostimulation, and/or photocollagen stimulation, on biological tissue. The apparatus includes at least one, but preferably a plurality of radiation energy sources structured to selectively emit radiation towards the biological tissue. The apparatus further includes an irradiation head assembly which includes an adjustable collector assemble structured to collect and redirect scattered and reflected radiation back to the treatment site, an adjustable collimator assembly structured to adjustably collimate the emitted radiation, and an adjustable focal length setting mechanism structured to securely set a desired focal length of the emitted radiation relative to the biological tissue. The apparatus may further include one or more beam splitter assemblies to either allow for greater treatment area coverage or for the purpose of treating two patents requiring the same treatment protocol simultaneously while employing only a single radiation energy source. Furthermore, this apparatus may include a multi-fiber array or a conventional laser combiner to either marry a plurality of different wavelengths or utilize the different wavelengths individually depending upon the requirements of the treatment modality, tissue type, and the specific treatment protocol required.

A control module is further provided and is operatively associated with the radiation energy source or sources, the collector assembly, the collimator assembly, and the adjustable focal length setting mechanism. In this regard, the control module is configured to provide precise control over the total amount of radiation emitted, as well as the wavelength and energy density of the radiation that affects the biological tissue.

In one embodiment of the present invention, each radiation energy source has an energy output in the range of approximately 1 mW to 25,000 milliwatts ("mW"), and utilizes a laser beam as the source of radiation energy. It is understood that there are numerous lasers currently available which are capable of providing the required radiation energy, many of which may be incorporated into the present invention. In addition to the use of laser beams with various radiation energy outputs, the present invention may employ laser beams generated by a variety of source materials including, but not limited to, semiconductor or solid state diodes, $CO_2$, or neodymium:yttrium-aluminum-garnet ("Nd:YAG"). Furthermore, the present invention may encompass the utilization of laser beams which generate radiation energy over a wide range of energy wavelengths including from approximately 400 nanometers ("nm") to 3,000 nm, and may be utilized as either targeting lasers or treatment lasers. Accordingly, a variety of specific energy densities can be achieved at a variety of wavelengths, at variety of absorption rates while maintaining the desired energy density and energy levels throughout a plurality of treatment ranges and over larger areas, thus allowing numerous treatment modalities to be performed with a single apparatus.

The present invention further provides that the emitted radiation is disposed relative to a transmission assembly, wherein the transmission assembly comprises an elongated configuration structured to direct substantially all of the radiation emitted from the plurality of the radiation energy sources to the biological tissue. The transmission assembly includes at least one, but preferably a plurality of fiber optic cables which must be at least equal in number to the number of radiation energy sources. The plurality of fiber optic cables of the transmission assembly are further disposed together in a single bundle. Each fiber optic cable has a proximal end and a distal end, wherein each proximal end is operatively associated with and disposed to receive the radiation emitted from one of the plurality of radiation energy sources. The distal end of each fiber optic cable is structured to terminate at a point proximate to the biological tissue. Further, each fiber optic cable is structured to receive the radiation emitted from no more than one radiation energy source at one time so the amount and wavelength of the radiation emitted to the biological tissue may be precisely controlled.

An illustrated embodiment of the present invention includes an irradiation head assembly which may comprise the adjustable collector assembly, the adjustable collimator assembly, and the adjustable focal length setting mechanism. The illustrated adjustable collector assembly includes a reflecting device or lens at the posterior of the assembly that facilitates in the reshaping and redirection of the reflected and scattered treatment radiation back onto the site of treatment. The entire collection assembly by shape form and function, increases the effectiveness of the radiation treatment by redirecting treatment radiation that would normally be lost and by increasing the safety for all who are in the treatment room by eliminating the risk of eye damage due to scattered or reflected radiation. The illustrated adjustable collimator assembly of the present invention includes an inlet aperture and an outlet aperture, the inlet aperture being structured to engage the distal end of each fiber optic cable of the transmission assembly. Moreover, the adjustable collimator assembly may include at least one, but preferably a plurality of adjustable collimators. Additionally, the adjustable collimator assembly of the present invention is preferably articulating and targetable. In at least one embodiment, the plurality of adjustable collimators are preferably disposed to engage one another in a series configuration, so that the combined radiation emitted from the plurality of radiation energy sources is collimated by the first collimator, which is further collimated by the second collimator, and continuing in a similar fashion through each adjustable collimator. Accordingly, an illustrated embodiment of the present invention includes a plurality of adjustable collimators engaged in series so the radiation emitted from the plurality of radiation sources may be adjustably collimated over a continuous range.

The irradiation head assembly may further comprise an adjustable focal length setting mechanism, which operatively engages the outlet aperture of the adjustable collimator assembly. Thus, in addition to the collimation of the radiation emitted from one or more radiation sources, the focal length of the emitted radiation beam may be adjusted and set to define a specific contact area or "spot size", prior to exposure of the biological tissue. The adjustable focal length setting mechanism is structured to set a plurality of focal lengths between the outlet aperture of the adjustable collimator assembly and the contact surface of the adjustable focal length setting mechanism. Further, the contact surface is structured to be disposed in direct contact with the patient, and typically in direct contact with the biological tissue being treated, except, of course, when subcutaneous treatment is being performed, in which case the biological tissue being treated may not be directly contacted. Thus, each of the plurality of focal length settings, in conjunction with the adjustment of the collimation and the angle at which the beam is transmitted, defines a specific contact area or "spot size" on the contact surface. This is partly due to the fact that once a focal length is set, the distance between the outlet aperture and the contact surface is a fixed value. In a preferred embodiment of the present invention, the adjustable focal length setting mechanism is structured to set a plurality of focal lengths over a continuous range. The adjustable focal length setting mechanism thus provides a means to adjust and set the contact area or "spot size" of the combined emitted radiation, thus allowing the energy density to be precisely controlled during exposure of the biological tissue, which permits treatment over a larger "spot size" than would safely be possible otherwise. Indeed, the ultimate adjustment of the adjustable collimator and the adjustable focal length setting mechanism may utilize high power lasers and convert their ablative energy, thereby providing either biostimulation, photo-stimulation, or photocollagen stimulation by reducing the energy density via an increase in the divergence of the laser beam, and, therefore, the "spot size" at the affected area, thus providing a safe and desired energy density.

The control module of the present invention may be structured to receive a plurality of predetermined treatment parameter inputs from the operator of the apparatus including, by way of example only, photo-stimulation mode, biostimulation mode, photocollagen stimulation mode and/or ablation mode, treatment type, time of exposure, contact area or "spot size", energy wavelength, and/or type of laser may be set. In accordance with these parameters, the control module may be structured to determine the correct radiation energy sources to employ, the correct adjustment of the adjustable collimator assembly, and/or the correct setting of the adjustable focal length setting mechanism. Of course, if one variable characteristic is pre-set, the control module may determine the remaining settings in accordance therewith. The correct settings of the device may be determined by a password protected algorithm utilized by the control module to determine the correct combination of settings required to provide the correct energy density to the biological tissue based upon the malady requiring treatment and level of severity, for example, low, medium or high, which are input by the operator. In an alternate embodiment, the password protected algorithm may be overridden to permit the operator to input each treatment parameter independently as may be required to meet specific treatment requirements. The basic equation utilized by the algorithm to determine energy density ("ED") is as follows:

$$ED(J/cm^2) = \frac{\text{radiation energy output (milliwatts)} \times \text{time of exposure (seconds)}}{1{,}000 \times \text{contact area (cm}^2\text{)}}$$

The energy density utilized for photo-stimulation may range from 0.1 to 2,400 $J/cm^2$, while photocollagen stimulation may utilize energy densities ranging from 2.0 $J/cm^2$ to 1,800 $J/cm^2$, and the energy density for ablation may range from 3000 $J/cm^2$ to 25,000 $J/cm^2$.

Once the correct settings have been determined, the plurality of radiation energy sources, the adjustable collimator assembly, the adjustable collector, and the adjustable focal length setting mechanism are either manually oriented in accordance with their correct settings or, in a preferred embodiment, automatically oriented by standard electro-mechanical control devices including, for example, a combination of electro-mechanical switches and servo-motors, to provide the correct energy density at the contact surface. The control module may also include software watchdogs and feedback loop algorithms structured to monitor and, in the automated embodiment, control the radiation emitted throughout the treatment process through the utilization of, for example, an infrared pick off sensor.

These and other features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a schematic representation of one embodiment of the present invention utilizing one radiation energy source and a beam splitter.

FIG. 2 is a schematic representation of another embodiment of the present invention utilizing two radiation energy sources.

FIG. 11 is a schematic representations of the control module of the present invention.

Like reference numerals refer to like parts throughout the several views of the drawings.

DETAILED DESCRIPTION OF THE PREFERRED EMBODIMENT

Figure 3:
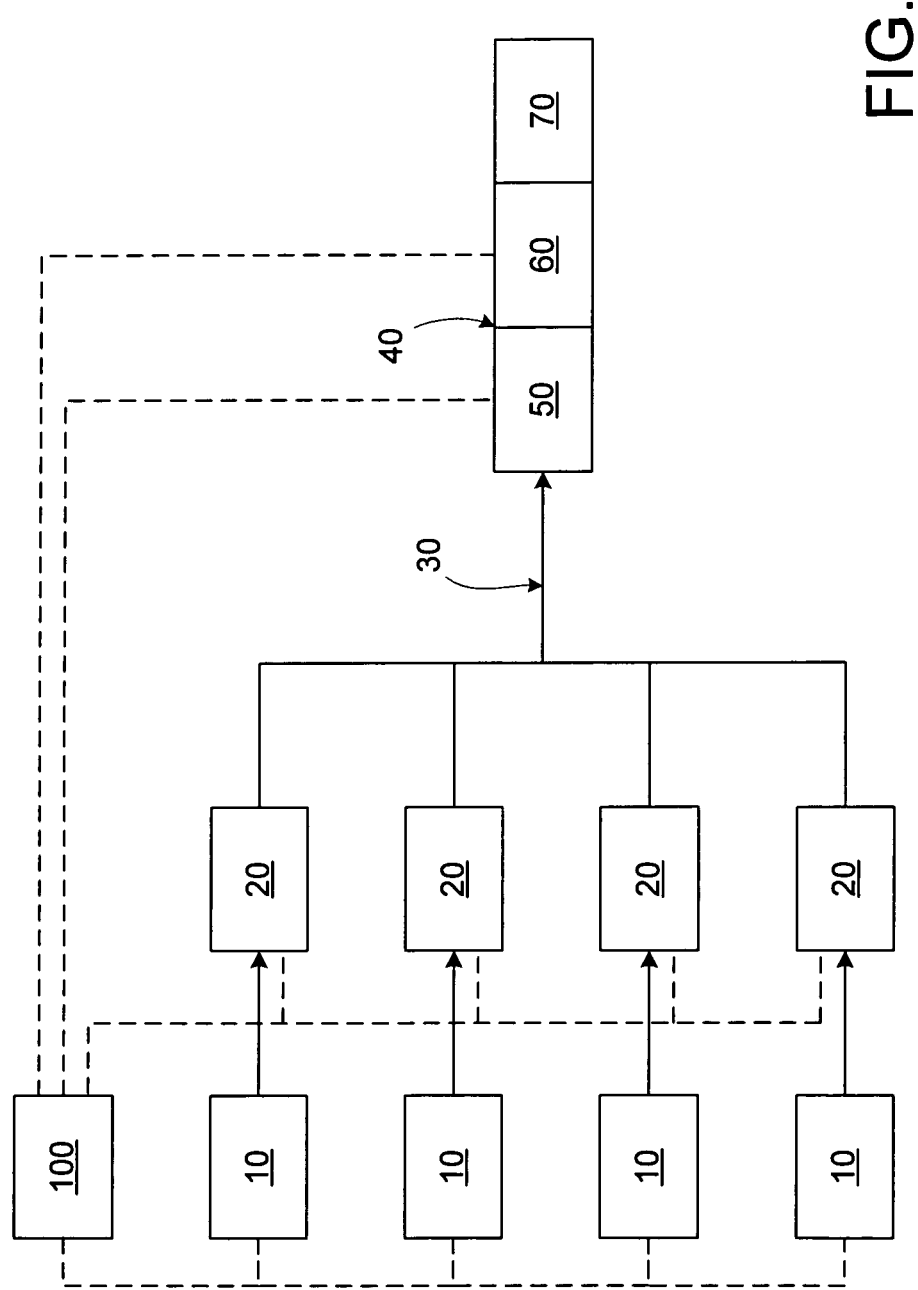
FIG. 3 is a schematic representation of another embodiment of the present invention utilizing four radiation energy sources.

As shown throughout the Figures, the present invention is directed to an apparatus and method for performing a plurality of radiation energy treatment, including at least photo-stimulation, biostimulation, photocollagen stimulation, and/or photobiostimulation, on biological tissue. The apparatus provides complete control of the energy density, area of treatment or "spot size", and allows the utilization of specific wavelengths alone or in combination, either coincidentally or adjacently, as required for optimal penetration and absorption characteristics to selectively treat a specific tissue type and obtain the most beneficial results. As shown in FIG. 1, the laser treatment apparatus includes a power supply, which is shown schematically as 10, for at least one radiation energy source, shown schematically as 20, wherein the radiation energy output by the radiation energy source 20 is received by a transmission assembly, generally shown as 30, which transmits the radiation energy to an irradiation head assembly, generally shown as 40, as illustrated in one embodiment in FIG. 4. The transmission assembly 30 is further structured to permit the transmission of radiation energy output by a plurality of radiation energy sources 20, as schematically illustrated in FIGS. 2 and 3.

The irradiation head assembly 40 preferably includes an adjustable collimator assembly 50, a collector assembly 80 and a focal length setting mechanism 60. Furthermore, the irradiation head assembly 40 is structured such that the angle at which the radiation energy is transmitted to the biological tissue may be adjustably set. In a preferred embodiment, the irradiation head assembly 40 may comprise a generally cylindrical shape, however, the assembly may comprise other forms as may be required, including but not limited to a conical shape. Moreover, the present invention may employ a control module 100 to determine, monitor, and, in one embodiment, automatically control the correct settings for one or more of the aforementioned components before and during operation of the laser treatment apparatus.

Figure 8:
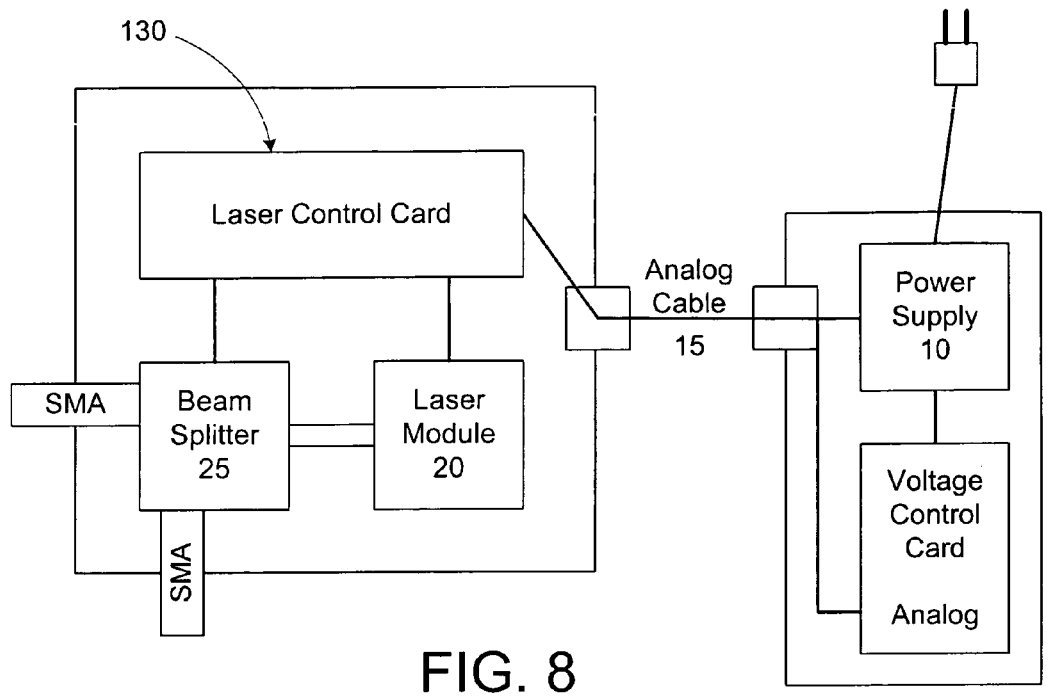
FIG. 8 is a side elevation view of one embodiment of the present invention wherein the size of the laser apparatus is reduced by a unique construction design that utilizes a beam spliter and at least one source of radiation.
Figure 9:
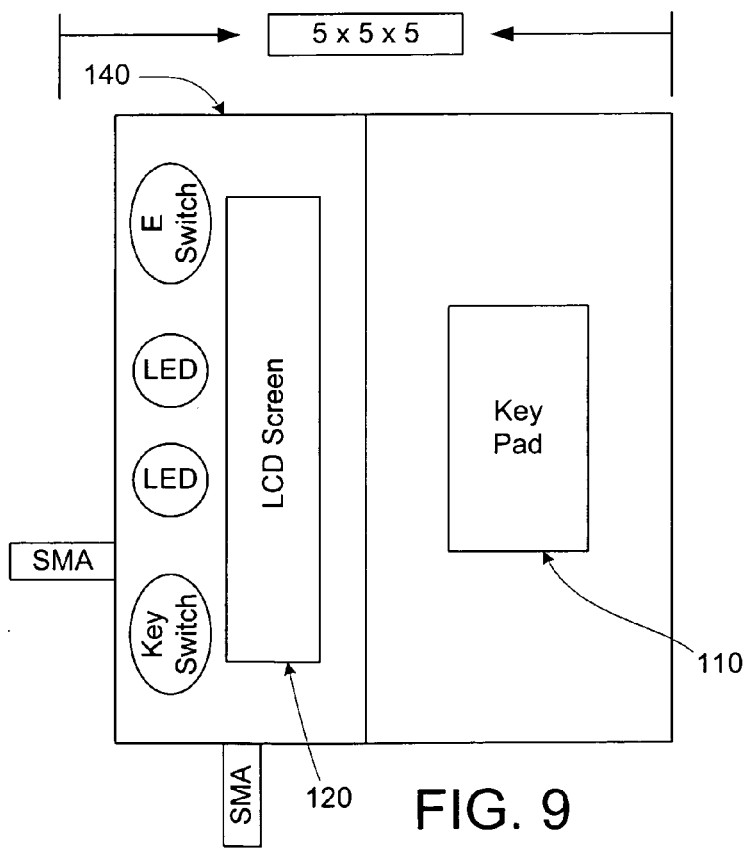
FIG. 9 is a side elevation view of an embodiment wherein the radiation source is contained in a compact case.

Looking further to the power supply 10 of the present invention, it is preferably utilized to activate the radiation energy source 20 during operation of the laser treatment apparatus. The power supply 10 may be integral with the radiation energy source 20, disposed in close proximity thereto, however, in a preferred embodiment, the power supply 10 and laser control card are remotely located yet operatively associated with the radiation energy source 20. This embodiment is presented in FIGS. 8 and 9. In this embodiment, the radiation source 20 only comprises the laser, laser controls 110, LCD Screen 120 and a laser control card 130 enclosed in a single compact case 140 measuring approximately 5×5×5 inches, such that the entire radiation energy source 20 is more compact and easier for an operator to maneuver. The power supply 10 and radiation energy source 20, in this preferred embodiment, are operatively associated by way of an analog cable 15 which includes connections for an analog TTL wire, a control signal, a drive signal, a current signal, a CPU ground and a chassis ground.

As indicated, the present invention may encompass a variety of radiation energy sources 20 with a wide range of radiation energy outputs, and, therefore, a wide range of power supplies 10 may be included. The power supply 10 in one embodiment of the present invention is an alternating current device to assure a constant, stable supply of power to the radiation energy source 20, although a direct current device for a portable apparatus is envisioned. Additional embodiments of the present invention include a power supply 10 which, in conjunction with the software and the voltage control card of the control module 100, is capable of supplying power to the radiation energy source 20 to permit a plurality of treatment types including at least CW, pulse, long-pulse (i.e. 10–55 milliseconds), pulsed arc-lamp pumped Nd:YAG 1064 or Q-switch pulse. Further, the power supply 10, once again in conjunction with the software and the voltage control card of the control module 100, may be capable of supplying power at frequencies ranging from approximately 0.1 to 200 cycles per second and having a pulse width of between 0.1 and 100 percent. This invention in addition to generating pulsed radiation in either cycle per second or in percentages as a duty cycle is structured to emit radiation pulses in a series of different steps that combine to become a cadence. As the output of the pulsed step within a cadence increases the duration of the off cycle within the cadence is also increased proportionally so that the desired effect is achieved and the biological tissue is not injured and its temperature remains below 40.7 C.

As indicated, the present invention further comprises at least one, but preferably a plurality of radiation energy sources 20, as shown in FIG. 2. The radiation energy sources may include low power, medium power, and/or high power radiation energy sources 20, thus each source utilized by the present invention may have an energy output at least in the range of approximately 0.1 to 25,000 mW. In FIG. 3, a preferred embodiment of the present invention utilizes various lasers as the radiation energy sources 20, and indeed, may incorporate a number of commercially available lasers meeting the energy output criteria of the present invention. Additionally, the present invention may incorporate lasers which generate radiation energy from a variety of different source materials including, but not limited to, semiconductor or solid state diodes, CO2, or Nd:YAG. As a result of the wide variety of source materials and types of lasers which may be employed, the present invention can generate radiation energy over a wide range of energy wavelengths including from approximately 400 nm to 3,000 nm, thereby providing the flexibility to effectively treat a variety of conditions with a single device.

As will be described in greater detail hereinafter, these various, varied lasers may be configured so as to overlap allowing a synergistic application to the treatment area, or they may be segregated to act simultaneously yet independently on different portions of the treatment area, or they may be utilized individually upon the treatment are, as needed. In particular, as a result of the adjustability and control attainable with the present invention, multiple types of radiation energy sources may be employed simultaneously as may be required to treat different conditions or work to together to treat different aspects of the same condition. As such, if desired, the outputs may be set to fixedly or adjustably overlap or be separate. When the outputs overlap, however, the total radiation energy output is summed, and the control module 100, as will be described, compensates for this increased energy output, such as by increasing the focal length, adjusting the collimation, increasing the divergence of the emitted radiation energy, adjusting the spot size, etc. The biological tissue is thereby not subjected to multiple treatments in many cases, and moreover, when complimentary treatments/lasers are available, they can effectively work together without fear of exceeding safe or desired energy densities.

Figure 7:
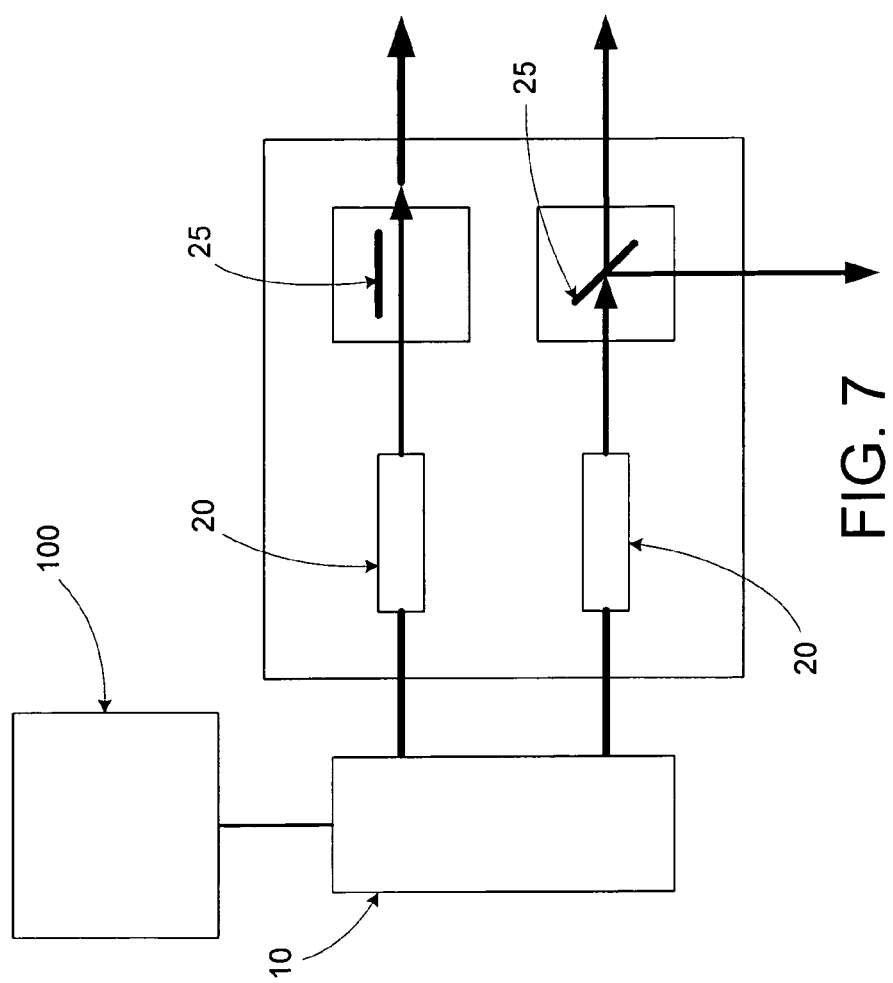
FIG. 7 is a side elevation view of one embodiment of the present invention utilizing two radiation energy source and two beam spliters to generate a combination of different treatment beams either simultaneously or individually.

One embodiment of the present invention further includes a beam splitter assembly, schematically shown as 25 in FIG. 1 and FIG. 7. The beam splitter assembly 25 comprises at least one adjustable dichromatic mirror which is positionable into and out of the path of the emitted radiation beam. A preferred embodiment utilizes a 50/50 dichromatic mirror structured such that when the mirror is placed at approximately a 45 degree angle incident to the emitted radiation beam, the beam splits into two components having energies approximately equal to one another and totaling the energy of the original emitted radiation beam. Accordingly, a single radiation energy source 20 may be split one time or several times thereby providing a plurality of emitted radiation beams which may be utilized for the treatment of a greater surface area than possible with a single beam. This embodiment provides the further advantage of allowing the practitioner to treat more than one patient at the same time with a single compact laser. Furthermore, this embodiment provides an additional advantage of reducing the size of the entire radiation energy source 20 which is more compact and easier for an operator to maneuver, as a result of utilizing a single laser in applications which previously required multiple laser sources.

Figures 4, 5:
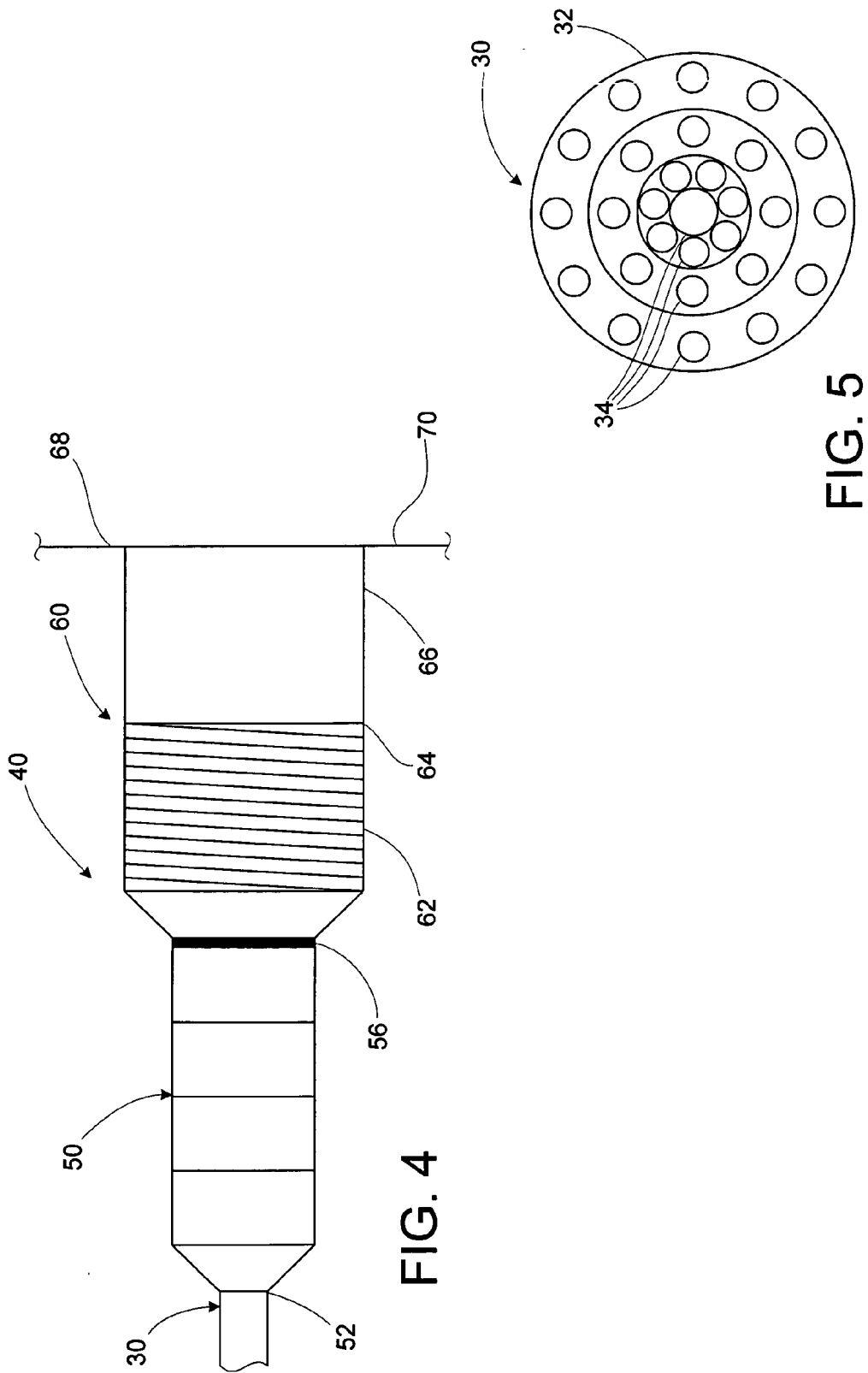
FIG. 4 is a side elevation view of one embodiment of the irradiation head assembly of the present invention.
FIG. 5 is a cross-sectional view of one embodiment of the transmission assembly of the present invention.

Turning to FIGS. 4 and 5, a preferred embodiment of the present invention includes at least one transmission assembly 30, either independently or as part of the irradiation head assembly 40. Preferably, the radiation energy sources 20 are disposed relative to the transmission assembly 30, which is structured to receive substantially all of the radiation energy output from the plurality of radiation energy sources 20 and to direct the emitted radiation proximate to the biological tissue. In one embodiment, the transmission assembly 30 comprises an elongated structure including at least one fiber optic cable 34, however, a preferred embodiment of the present invention may include a plurality of fiber optic cables 34. In such an embodiment, each fiber optic cable 34 has a proximal end and a distal end, wherein each proximal end is disposed relative to the radiation energy source or sources. At least one fiber optic cable 34 is provided for each radiation energy source 20, wherein each proximal end is disposed to only receive radiation energy output from a single radiation source 20 at one time. This allows precise control over the amount and the wavelength of the radiation energy transmitted by the transmission assembly 30.

In the illustrated embodiment, the distal end of each fiber optic cable 34 terminates proximate to the biological tissue, such as at the irradiation head assembly 40 which includes the adjustable collimator and aspheric collimator lens which comprise assembly 50, or further energy processing components thereof. In a preferred embodiment of the present invention, the distal end of each fiber optic cable 34 of the transmission assembly 30 engages an inlet aperture 52 of the adjustable collimator assembly 50. As previously noted, in a preferred embodiment, the transmission assembly 30 is structured to receive and transmit substantially all of the radiation energy output from the plurality of radiation energy sources 20. Therefore, the emitted radiation entering through the inlet aperture 52 of the adjustable collimator assembly 50 is the combination of the emitted radiation from each of the radiation sources 20 activated.

As illustrated in FIG. 5, a preferred embodiment of the transmission assembly 30 of the present invention comprises a series of fiber optic cables 34 concentrically arranged in a single bundle 32. In this configuration, any one or more of the fiber optic cables 34 may be utilized to transmit emitted radiation from any one or more of the plurality of radiation energy sources 20. This allows the simultaneous transmission of radiation energy from the same or separate beams, and having different energies and/or wavelengths, to the biological tissue utilizing a single transmission assembly 30. By way of example, utilizing the transmission assembly 30 of the present invention, the operator may perform photostimulation, photocollagen stimulation and/or ablation on the biological tissue at the same time utilizing the same device. Additionally, the preferred embodiment of the transmission assembly 30 allows radiation energy of various wavelengths which may be utilized for either aiming or treatment to be transmitted simultaneously. When a radiation energy source 20 is utilized for aiming purposes, it is emitted coincident with all other radiation energy output, including that which may be outside the visible spectrum, such that the entire amount of radiation energy output may be precisely targeted.

Figure 6:
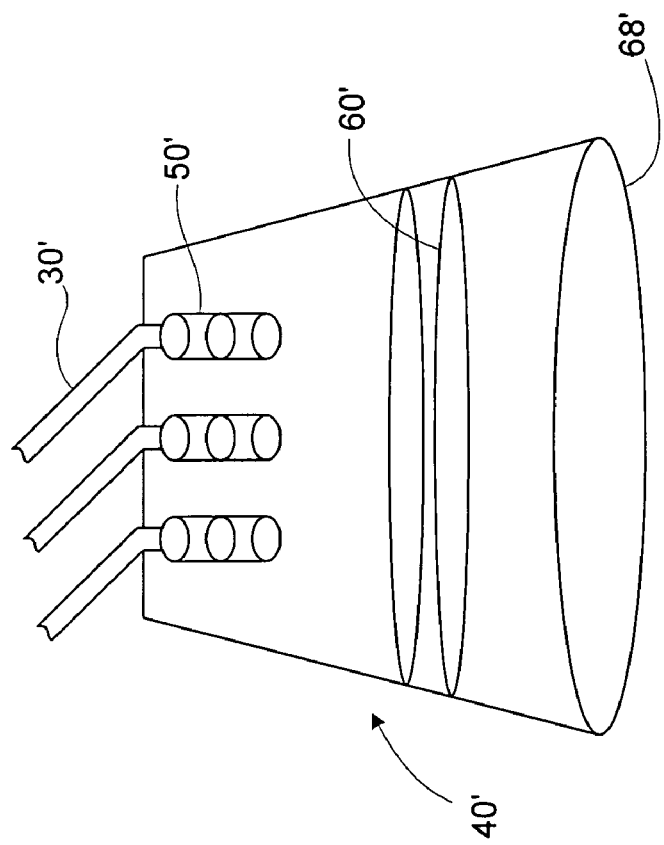
FIG. 6 is a front elevation view of an embodiment of a modified irradiation head assembly.

Returning to FIG. 4, the adjustable collimator assembly 50 includes at least one adjustable collimator, however, a preferred embodiment of the present invention comprises a plurality of adjustable collimators disposed to engage one another in a series configuration as illustrated in FIG. 6. Further, a preferred embodiment of the present invention comprises a plurality of adjustable collimators that are both articulating and targetable. Each collimator may be adjusted either manually or automatically. The arrangement of adjustable collimators in series allows the combined radiation emitted to be collimated over a wide, continuous range, although in some embodiments the adjustability provided by a single collimator may suffice. The series arrangement of adjustable collimators is beneficial so that the amount and the wavelength of the combined radiation energy output from the outlet aperture 56 of the adjustable collimator assembly 50 may be precisely controlled. Thus, the adjustable collimator assembly 50 allows precise control over one of the parameters which defines the energy density at the discharge of a radiation energy source. Additionally, the adjustable collimator assembly 50 allows the radiation energy to be articulated and precisely targeted at the biological tissue requiring treatment.

Also in a preferred embodiment of the present invention, the adjustable collimator assembly 50 is operatively engaged with the control module 100, wherein each adjustable collimator is oriented into position in accordance with the correct settings determined by the control module 100. These correct settings are preferably determined based on the treatment parameters input by the operator, the collimator(s) being adjustable manually, or automatically by standard electro-mechanical control devices including, by way of example only, electro-mechanical switches and servo-motors. The orientation of the adjustable collimator assembly 50 based on the correct settings determined by the control module 100, whether manually or automatically, minimizes the potential for operator error, and thus provides the correct amount and wavelength of radiation energy at the outlet aperture 56 of the adjustable collimator assembly 50. Furthermore, if the user wishes to preset a particular configuration of the adjustable collimator assembly 50, the control module 100 is able to compensate accordingly utilizing the settings for the remaining components.

Figure 10:
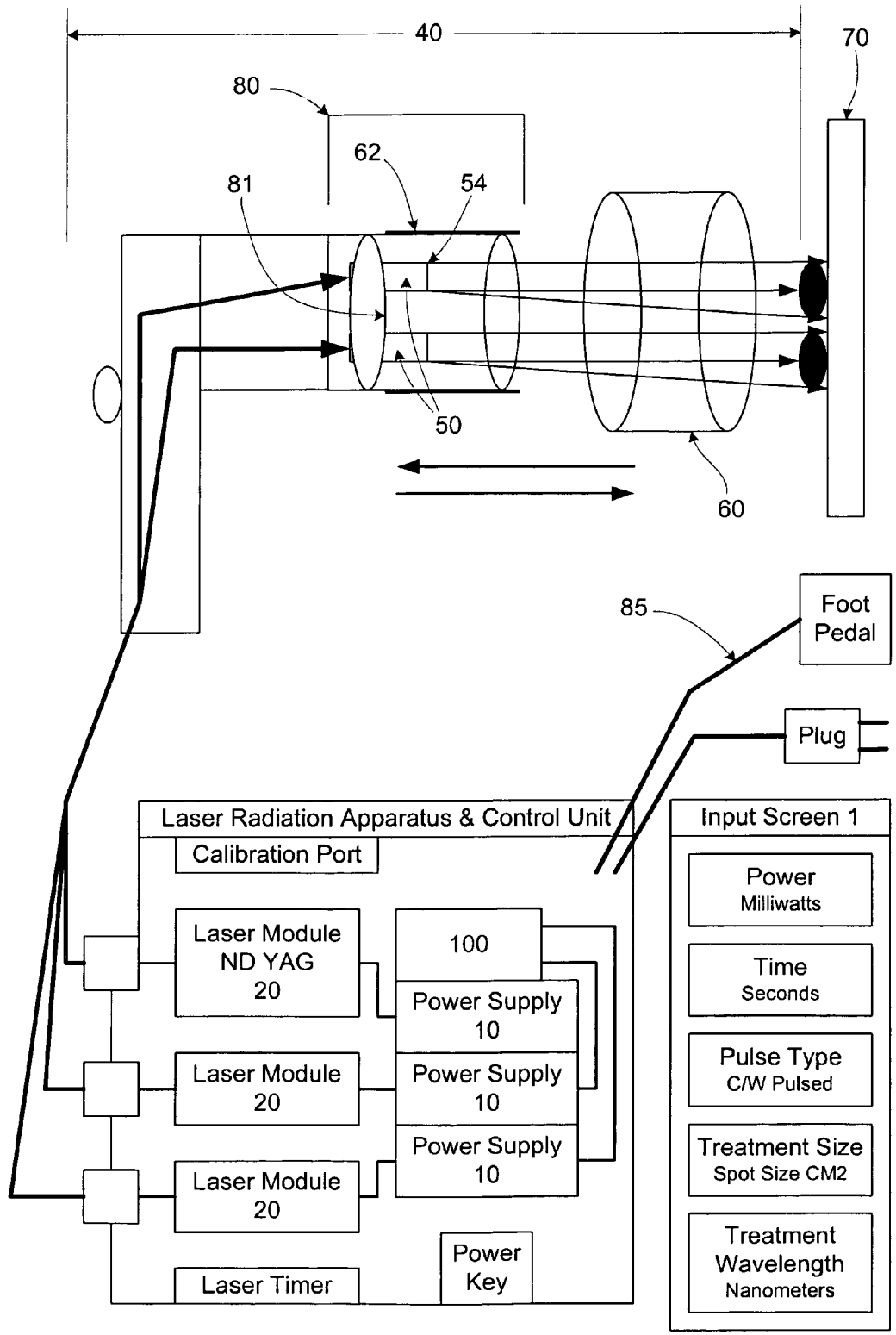
FIG. 10 is a schematic representation of another embodiment of the present invention utilizing three radiation energy sources and an input screen.
Figure 12A:
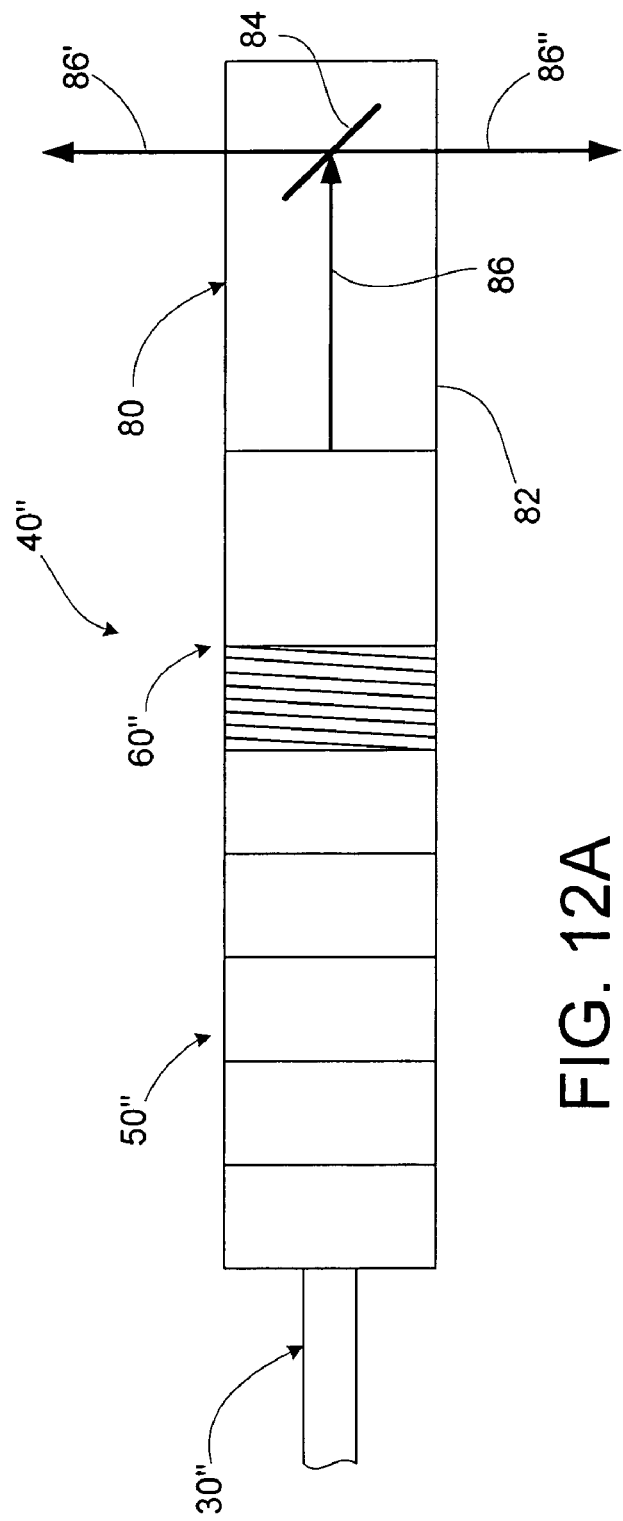
Figure 12B:
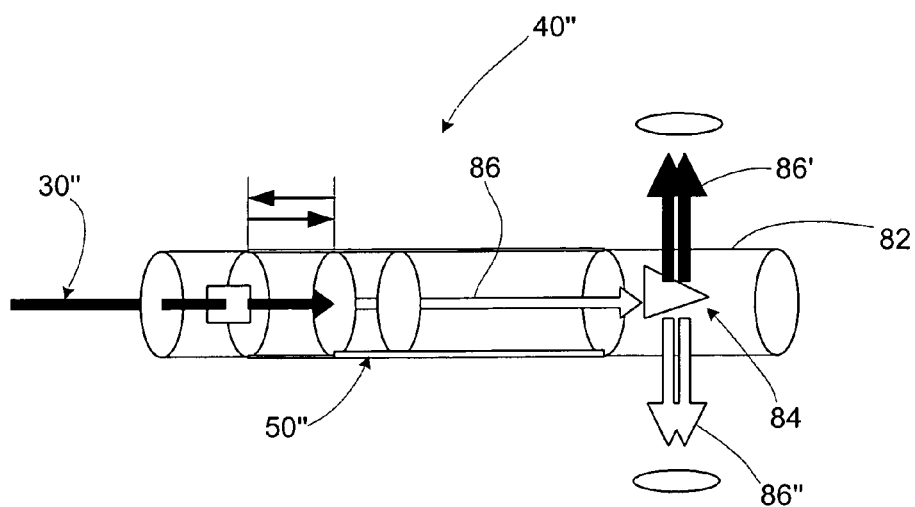
Figure 12C:
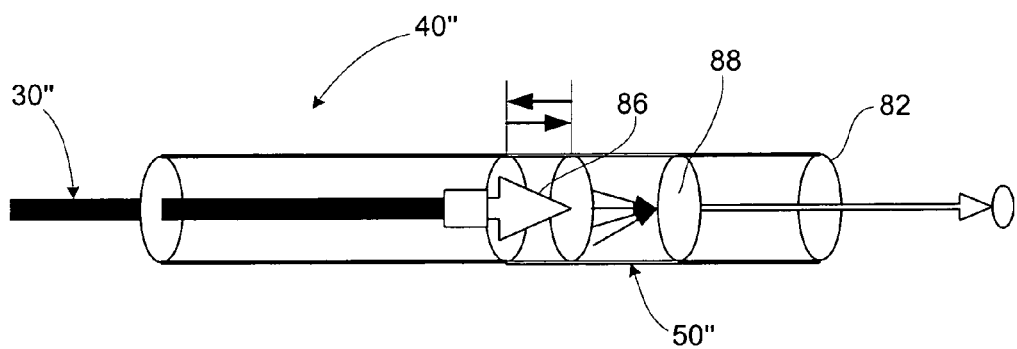
Figure 12D:
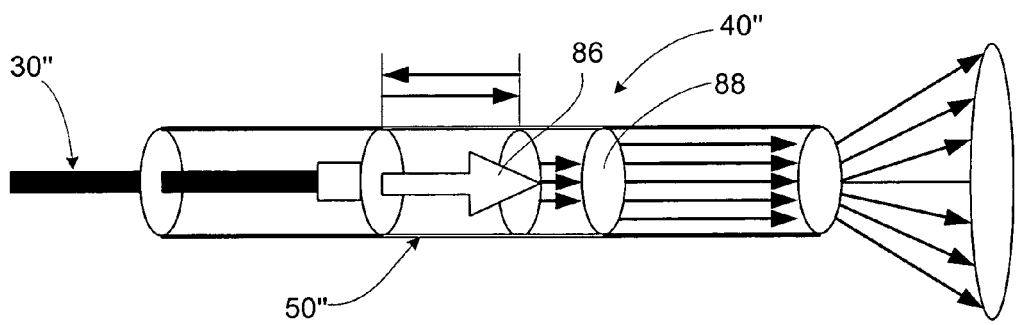
Figure 12E:
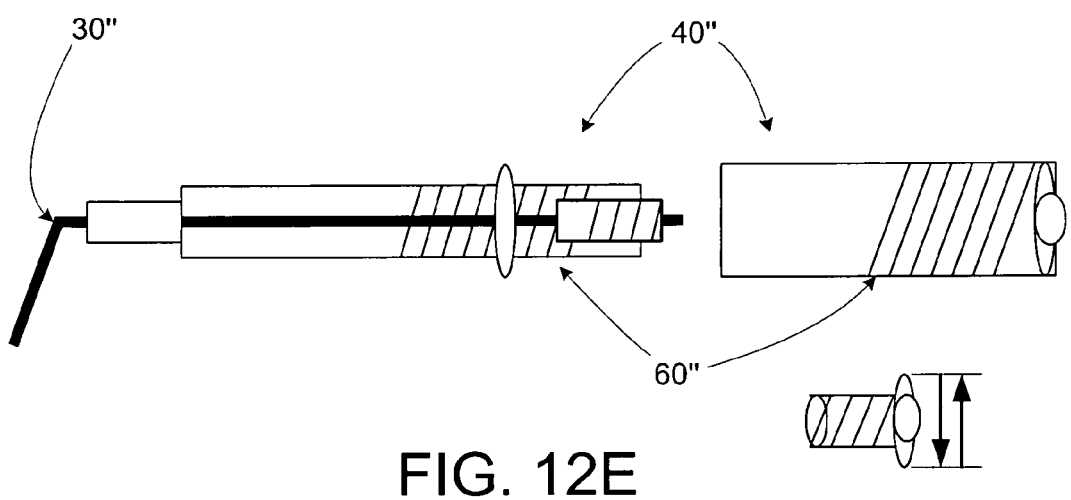

Turning to FIG. 10, the present invention further includes a collector assembly 80 and a reflecting assembly 81. The collector assembly 80 collects the reflected and scattered radiation and directs the collected radiation onto the reflecting assembly whereby it is reflected back to the original treatment site. The threaded outer surface of the collector sleeve 62 operatively engages the inner threaded sleeve of the adjustable focal length assembly 66 thereby allowing precise adjustment of the working distance between the between the outlet aperture 56 and the contact surface 68.

As indicated, the present invention further includes an adjustable focal length setting mechanism 60. The adjustable focal length setting mechanism 60 may be operatively engaged with the outlet aperture 56 of the adjustable collimator assembly 50, although reverse orientation is possible, and as such the single or combined source of radiation emitted from the adjustable collimator assembly 50 is transmitted to the adjustable focal length setting mechanism 60. The adjustable focal length setting mechanism 60 is operatively associated with the collector sleeve 62 which is disposed generally at the outlet aperture 56 of the adjustable collimator assembly 50. In addition, the collector sleeve 62 may include at least one coated lens which initially focuses the combined emitted radiation prior to exposure to the biological tissue.

In the illustrated embodiment, the adjustable focal length setting mechanism 60 further includes an adjustable focal length body 66 (FIG. 6), operatively associated with the collector sleeve 62. The adjustable focal length body 66 includes a focal length lug 64 which operatively engages the collector sleeve 62 and the adjustable focal length body 66, and is moveably and fixedly positionable along at least a segment of the collector sleeve 62, either manually or automatically. In one embodiment, as illustrated in FIG. 4, the collector sleeve 62 is threaded to provide a means for moveably and fixedly positioning the adjustable focal length body 66. The adjustable focal length body 66, in a preferred embodiment, may comprise a substantially cylindrical configuration constructed of a coated plexiglass material to redirect reflected and/or scattered radiation to the treatment area.

The adjustable focal length body 66 may also include at least one coated lens which is operatively associated with the coated lens or lenses of the collector sleeve 62. The coated lenses allow the single or combined source of radiation emitted to be focused in a contact area or "spot size" which defines a specific area on the contact surface 68 of the adjustable focal length setting mechanism 60. The contact surface 68, as the name suggests, is structured to be placed in direct contact with the surface 70 of the treatment region of a patient during operation of the laser treatment apparatus. An increase in the distance between the coated lenses of the collector sleeve 62 and the adjustable focal length body 66 will increase the divergence of the beam, thereby increasing the contact area or "spot size". Conversely, a decrease in the distance between the coated lenses necessarily decreases the divergence of the beam, thereby decreasing the contact area or "spot size". In a preferred embodiment, the adjustable focal length adjustment assembly 60 is structured so the combined radiation emitted may be focused on the contact surface 68 over a wide and continuous range of focal lengths, thereby defining a wide and continuous range of contact areas or "spot sizes". Thus, the adjustable focal length setting mechanism 60 permits the divergence of the beam, and, therefore, the contact area or "spot size" to be precisely set and controlled for the single or combined source of radiation emitted, which allows precise control of the other parameter which defines the energy density at the discharge of the radiation energy source.

Further, the adjustable focal length setting mechanism 60 may be operatively engaged with the control module 100, wherein the adjustable focal length body 66 is automatically oriented into position along the collector sleeve 62 by any standard electro-mechanical control devices including, but not limited to, a combination of electro-mechanical switches and servo-motors. The orientation of the adjustable focal length body 66 based on the correct settings as determined by the control module 100, whether manually or automatically, further minimizes operator error in defining the correct contact area or "spot size" on the contact surface 68 of the adjustable focal length setting mechanism 60. This also permits a larger "spot size" to be set, through greater divergence of the beam, while still achieving safe and precise operating conditions.

Therefore, utilizing the control module 100, and the combination of the adjustable collimator assembly 50 and the adjustable focal length setting mechanism 60, the present invention is capable of providing precise control of the energy density at the contact surface 68, which subsequently permits precise control of the energy density on the biological tissue. Additionally, the present invention is capable of providing precise control of the energy density on the biological tissue for a wide range of radiation energy sources comprising different energy outputs and various energy wavelengths, thereby allowing a variety of treatments to be performed utilizing the single apparatus of the present invention.

The present invention further encompasses the utilization of a modified irradiation head assembly 40' which comprises a plurality of adjustable collimator assemblies 50', which may be both articulating and targetable, each being supplied by a separate transmission assembly 30', as illustrated in FIG. 6. As shown, this embodiment utilizes a single adjustable focal length setting mechanism 60' for each of the plurality of adjustable collimator assemblies 50', which thereby focuses each emitted radiation source on a single contact surface 68'. This embodiment is designed to further facilitate the performance of photo-stimulation, photocollagen stimulation and/or ablation simultaneously yet independently on different portions of the treatment area with a single apparatus. A further variation of this embodiment provides a plurality of irradiation head assemblies 40 assembled into one or more earpieces which are mounted on a headpiece. This configuration may be utilized to photostimulate areas of the inner ear to alleviate tinnitus, unstable balance, and other related conditions.

As illustrated in FIG. 12 an alternate embodiment of the present invention is structured and disposed specifically to permit at least photo-stimulation, photo-dynamic therapy and/or ablation radiation energy treatment to be performed invasively. In this embodiment, the irradiation head assembly 40" is disposed in an adjustable catheter and comprises an adjustable dichromatic mirror assembly 80 which is operatively engaged in series with the adjustable focal length setting mechanism 60" and the adjustable collimator assembly 50". In a preferred embodiment, the adjustable dichromatic mirror assembly 80 includes a clear coated acrylic housing 82 structured to transmit infrared radiation energy. In this embodiment of the present invention, the transmission assembly 30" and each component of the adjustable catheter irradiation head assembly 40" comprise a substantially reduced physical size to permit the entire adjustable catheter irradiation head assembly 40" to be inserted into an artery, vein, or other internal region of a patient requiring treatment.

The present invention further comprises a method for performing radiation energy treatment, such as photo-stimulation, photocollagen stimulation and/or ablation, utilizing the laser treatment apparatus disclosed herein. Therefore, the present method allows an operator to apply radiation energy treatment to a group of cells, a collection of tissue, or an entire organ, based upon the operator selected treatment parameters input. The present method further employs a variety of radiation sources providing a plurality of energy wavelengths which may be utilized, either separately or simultaneously, to stimulate different chromophores within the organism undergoing treatment due in part to the fact that different energy wavelengths have different absorption characteristics. Furthermore, the method of the present invention allows the operator to not only apply but to control precisely the radiation energy that is applied in all three dimensions and to penetrate up to four centimeters of tissue non-invasively. With respect to photo-stimulation, the effect of the radiation energy treatment is an increase in blood flow as a result of an increase in the amount of singlet oxygen and nitric oxide in the body, which are produced as photons are absorbed. This further results in an increase in sodium dissmutase and ATP production within the cells, and also increases fibroblast, osteoblast, fibrinogen, keratinocyte, macrophage, and endorphin production. The present method may be utilized in the treatment of numerous maladies including, by way of example only, soft tissue repair, pain management, and wounds, as well as providing relief from the symptoms of acquired immune deficiency syndrome ("AIDS"), herpes simplex, viral infections, reflex sympathetic dystrophy, muscular dystrophy, fibromyalgia and multiple sclerosis, based upon the operator selected treatment parameters. A plurality of specific treatment protocols may be utilized to affect treatment of a number of specific maladies utilizing the apparatus and method of the present invention, however, it is stressed that the apparatus and method of the present invention are not in any manner limited to affecting treatment of these specific maladies.

The first step in the method is the selection of one or more treatment parameters for the operator of the laser treatment apparatus from a plurality of predetermined treatment parameters. The predetermined treatment parameters may include, but are not limited to, photo-stimulation mode, photocollagen stimulation mode and/or ablation mode, radiation energy output, treatment type (i.e. CW, pulse, long-pulse, pulsed arc-lamp pumped Nd:YAG 1064 or Q-switch pulse), time of exposure, contact area or "spot size", energy wavelength, focal length, collimation, etc.

Next, the selected parameters are input to the control module 100 by the operator of the laser treatment apparatus. The control module 100 then determines the correct combination of radiation energy sources 20, the correct settings for each adjustable collimator of the adjustable collimator assembly 50, and the correct setting of the adjustable focal length setting mechanism 60 to assure the correct energy density is provided at the contact surface 68, based on the treatment parameters selected and input. Each component of the laser treatment apparatus is then either manually or automatically oriented into position in accordance with the correct settings determined by the control module 100.

After the selected treatment parameters are input to the control module 100, and the components are oriented in accordance with their respective correct settings, the irradiation head assembly 40 is placed into position relative to the surface 70 of the treatment region of the patient, which in a preferred non-invasive biostimulation embodiment is determined when the contact surface 68 is in direct contact with the surface 70. In one embodiment, an activation code must be input to the control module 100 to activate the laser treatment apparatus, thus initiating the treatment process. Once the treatment process has been initiated, the irradiation head assembly 40 is maintained in position relative to the surface 70 of the treatment region of the patient until the control module 100 deactivates the laser treatment apparatus upon completion of the selected treatment process. In another embodiment, the treatment parameters are pre installed within the control module and there are specific protocols for each malady that constitute a treatment regimen. Futhemore, there are a plurality of pre installed treatment regimens that are specific to a certain type of treatment, for example biostimulation, that constitute a treatment modality. In this way the radiation treatments will be completely safe for the patent and the results will be uniform. In this embodiment the independent variables and possible errors are dramatically reduced and the practitioners efficiency and patents treatment results are greatly increased.

The method of the present invention may include, in an alternate embodiment, the placement of a cold device proximate to the biological tissue. The method may utilize any of a number of cold devices structured for application to an area of biological tissue such as, by way of example only, a standard ice pack, cold chemical pack, chemical spray or an electronically controlled refrigeration device. The cold device is utilized to effectively lower the temperature of the biological tissue such that the tissue is able to accept more radiation energy than it would at ambient temperature. Regardless of whether or not the cold pack device is employed, when the selected treatment mode is photo-stimulation, at no time is the temperature of the tissue in the treatment area to exceed approximately 40 degrees Celsius, at which point proteins begin to denature.

The present method may be utilized in the treatment of numerous maladies including, by way of example only, soft tissue repair, pain management, and wounds, as well as providing relief from the symptoms of acquired immune deficiency syndrome ("AIDS"), herpes simplex, viral infections, reflex sympathetic dystrophy, muscular dystrophy, fibromyalgia and multiple sclerosis, based upon the operator selected treatment parameters. Table 1 contains a brief summary of sample treatment protocols which may be utilized to affect treatment of a number of specific maladies utilizing the apparatus and method of the present invention, however, it is stressed that the apparatus and method of the present invention are not in any manner limited to affecting treatment of any additional maladies which may not be specifically listed in Table 1.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Insert Radiation Treatment Chart

Now that the invention has been described,

What is claimed is:

1. A method for performing radiation energy treatment on a treatment site of biological tissue, said method comprising:

generating radiation energy having a power of between 0.1 and about 25,000 milliwatts;

wherein said generating includes generating at least one treatment radiation at a wavelength between 425 nm and about 1290 nm and at least one targeting beam with a wavelength between 400 nm and 760 nm coincident with the at least one treatment radiation;

emitting radiation energy towards the treatment site using an adjustable irradiation head assembly including an adjustable collector to collect scattered and reflected radiation from the treatment site and redirect the collected radiation back to the treatment site, at least one adjustable collimator to adjustably collimate the emitted radiation energy, and at least one focal length setting mechanism that sets the focal length of emitted radiation energy;

conducting the at least one treatment radiation through the adjustable irradiation head assembly that is structured to provide a plurality of adjustments and to focus the treatment radiation over a continuous range;

placing the adjustable irradiation head assembly in a treatment position so that it emits radiation energy to the treatment site for a therapeutically effective treatment time of between 1 second and about 3600 seconds; and controlling the emitted radiation energy with a control module that is operatively associated with said radiation energy and said adjustable irradiation head assembly;

wherein the treatment radiation is emitted in a plurality of cadences that are structured to increase the energy density of the pulses within the cadences while proportionally increasing the duration of the off cycles within said cadence, whereby the depth penetration of the treatment radiation will be increased by the increased energy density of the pulses within the cadences while the temperature of the biological tissue will not exceed 40.7 centigrade.

* * * * *